United States Patent [19]

Nakano et al.

[11] Patent Number: 5,446,110
[45] Date of Patent: Aug. 29, 1995

[54] CARBONATE MODIIED POLYESTER POLYOL

[75] Inventors: Shinji Nakano, Takatsuki; Takao Morimoto, Matsubara; Shin-ya Yamada, Sakai; Takaaki Fujiwa, Otake; Hideki Matsui, Otake; Takeharu Tabuchi, Otake, all of Japan

[73] Assignees: Nippon Paint Co., Ltd.; Diacel Chemical Industries, Ltd., both of Osaka, Japan

[21] Appl. No.: 359,832

[22] Filed: Dec. 20, 1994

Related U.S. Application Data

[62] Division of Ser. No. 159,605, Dec. 1, 1993.

[30] Foreign Application Priority Data

Dec. 1, 1992 [JP] Japan ............................ 4-3453333
Oct. 28, 1993 [JP] Japan ............................ 5-294509

[51] Int. Cl.[6] ............................................ C08F 8/14
[52] U.S. Cl. ............................. 525/439; 525/328.8; 525/384
[58] Field of Search ............................... 525/439

[56] References Cited

U.S. PATENT DOCUMENTS

| | | | |
|---|---|---|---|
| 2,863,854 | 12/1958 | Wilson | 525/439 |
| 3,426,100 | 2/1969 | McDonough | 525/439 |
| 3,657,191 | 4/1972 | Titzmann et al. | 525/439 |
| 3,966,788 | 6/1976 | Senet et al. | 525/439 |
| 4,217,297 | 8/1980 | Lindner et al. | 525/439 |
| 4,526,956 | 7/1985 | Mark | 525/439 |

Primary Examiner—Bernard Lipman
Attorney, Agent, or Firm—Millen, White, Zelano & Branigan

[57] ABSTRACT

A hydroxy-terminated linear carbonate is produced by reacting a cyclic alkylene carbonate such as neopentyl glycol carbonate with a substance having at least one alcoholic hydroxyl group in the presence of a catalyst. Mono- or polyhydric alphatic alcohols, polycaprolactone polyols, hydroxyl group-containing acrylic monomers and polymers, and polyester polyols are modified by the reaction with the cyclic alkylene carbonate to have an enhanced reactivity and resistance to hydrolysis.

5 Claims, No Drawings

CARBONATE MODIFIED POLYESTER POLYOL

This is a division of the application Ser. No. 08/159,605 filed Dec. 1, 1993.

BACKGROUND OF THE INVENTION

This invention relates to the synthesis of a hydroxy-terminated linear carbonate by reacting a compound or polymer having one or more alcoholic hydroxyl groups with a cyclic alkylenecarbonate.

It is known that when a compound having one or more hydroxyl groups is reacted with a cyclic alkylenecarbonate, the hydroxyl group is converted into a hydroxy-terminated alkylcarbonate group by the addition of the cyclic alkylenecarbonate moiety to the hydroxyl group.

Japanese Laid Open Patent Application (Kokai) No. 563.24/1980 discloses a process for producing a linear polycarbonate oligomer or polymer having a terminal hydroxyl groups by reacting a glycol with a cyclic alkylenecarbonate. A series of reactions takes place in this process. Firstly, the cyclic alkylenecarbonate is ring-opened with the glycol to produce a linear carbonate containing both of the hydrocarbon moieties corresponding to the glycol and cyclic carbonate reactants. Then, a transesterification occurs between the linear carbonate and the glycol with the formation of an alkylene glycol corresponding to the cyclic alkylenecarbonate as a by-product. The above reaction sequence continues to take place until the linear polycarbonate is chain-extended to a desired length. This process must be carried out under high vacuum to remove the alkylene glycol by-product from the reaction system. Therefore, the cyclic alkylenecarbonate used in the process is comparable, as a reactive derivative of carbonic acid, to phosgene conventionally used in the synthesis of polycarbonate polymers.

SUMMARY OF THE INVENTION

We have now discovered a new method in which a cyclic alkylenecarbonate may be addition reacted with or addition polymerized to a compound or polymer having one or more alcoholic hydroxyl groups while avoiding the formation of a glycol corresponding to the cyclic alkylenecarbonate as a reaction by-product. Therefore, the resulting linear carbonates are terminated with one or more linear hydroxyalkylcarbonate groups corresponding to the cyclic alkylenecarbonate. Since the terminal hydroxyl group is spaced apart from the backbone moiety by the linear carbonate linkage, the hydroxy-terminated linear carbonate is highly reactive and refractory to hydrolysis. Using these unique properties, alcoholic hydroxyl group-containing compounds or polymers used in the polyurethane or coating industry may be modified to have enhanced reactivity and resistance to hydrolysis.

In one aspect, the present invention provides a process for producing a hydroxy-terminated linear carbonate comprising reacting a 5-7 membered cyclic alkylenecarbonate and a substance having at least one alcoholic hydroxyl group in the presence of a catalyst selected from the group consisting of a Bronsted acid, an onium salt of a Bronsted acid anion, a strongly acidic cation exchange resin, an alkyl alkali metal, an alkali metal alkoxide, an amine, a tungsten compound, a tin compound, a titanium compound and a zinc compound.

In another aspect, the present invention provides a hydroxy-terminated linear carbonate of Formula I:

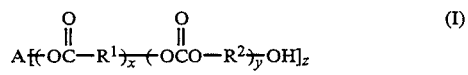

wherein A is an aliphatic hydrocarbon residue of up to 20 carbon atoms optionally containing etherical linkage, $R^1$ and $R^2$ are independently an alkylene having 2 to 8 carbon atoms, x is O or an integer of 1-6, y and z are independently an integer of 1-6.

In a further aspect, the present invention provides an acrylic monomer of Formula II:

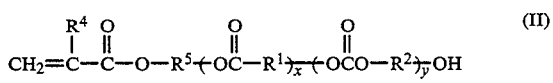

wherein $R^1$, $R^2$, x and y are as defined above, $R^4$ is hydrogen atom or methyl, and $R^5$ is an alkylene having 2 to 8 carbon atoms.

In still another aspect, the present invention provides an acrylic polymer having a recurring unit of Formula III:

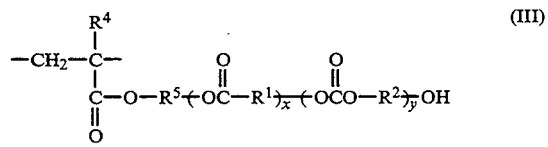

wherein $R^1$, $R^2$, $R^4$, $R^5$, x and y are as defined above.

In still another aspect, the present invention provides a modified polyester polyol of Formula IV:

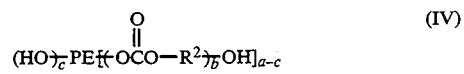

wherein PE is the residue of a polyester polyol with removal of the hydroxyl groups, $R^2$ is as defined, a is an integer from 2-15, b is an integer of 1-6, and c is an integer satisfying the relationship $0 \leq c < a$.

DETAILED DISCUSSION

The reaction involved in the process of the present invention may be regarded as an addition or addition polymerization reaction of a cyclic alkylenecarbonate using an alcoholic hydroxyl group-containing substance as an active hydrogen-containing initiator.

Cyclic Alkylenecarbonate

The cyclic alkylenecarbonate used in the process of the present invention is a 5-7 membered cyclic carbonate of a $C_2$-$C_8$ alkylene glycol and may be represented by Formula V:

wherein $R^2$ is a $C_2$-$C_8$, alkylene. The cyclic alkylenecarbonate may be produced by reacting a glycol and a dialkylcarbonate followed by depolymerizing the resulting polymer as disclosed in Japanese Laid Open (Kokai) Patent Application No. 56356/1990. Alternatively, the cyclic carbonate may be produced by reacting a corresponding alkylene oxide with carbon dioxide. The cyclic carbonate may form a 5–7 membered ring and contain 2 to 8 carbon atoms exclusive of the carbonate carbon atom. Specific examples thereof include ethylenecarbonate, as 5-membered ring carbonate, 1,3-propylene carbonate and neopentyl glycol carbonate also named 5,5-dimethyl-1,3-dioxan-2-one as 6-membered ring, and 1,4-butanediol carbonate as 7-membered ring. Neopentyl glycol carbonate is preferable because this compound may be easily synthesized in relatively short steps from commercially available raw materials. Moreover, this compound is normally stable but may react with an initiator in the presence of a catalyst under relatively mild conditions.

Initiators

The first class of initiators includes an aliphatic hydroxy compound of Formula VI:

wherein A is an aliphatic hydrocarbon residue of up to 20 carbon atoms optionally containing etherial linkage, $R^1$ is an alkylene having 2 to 8 carbon atoms, x is 0 or an integer of 1–6, and z is an integer of 1–6. The aliphatic hydroxy compound may be a mono- or polyhydric alcohol or its adduct with a $C_3$–$C_9$ alkanoic lactone such as ε-caprolactone.

Typical examples of monohydric aliphatic alcohols are $C_1$–$C_{20}$ alkanols such as methanol, ethanol, propanol, isopropanol, hexanol, 2-ethylhexanol, lauryl alcohol, stearyl alcohol and the like. The term "alphatic" as used herein refers to a compound whose hydroxyl group is directly attached to an aliphatic carbon atom. Accordingly, examples of monohydric aliphatic alcohols include benzyl alcohol, phenethyl alcohol, cyclohexanol, 3,3,5-trimethylcyclohexanol and the like. Also included are monohydric aliphatic alcohols containing etherial linkage and/or unsaturated bond such as methoxypropanol, 3-methoxybutanol, ethylene glycol monomethyl or monoethyl or monobutyl ether, triethylene glycol monoethyl ether, glycidol, allyl alcohol, hydroxyethyl vinyl ether, hydroxybutyl vinyl ether, ethylene glycol monoallyl ether, propargyl alcohol and hydroxyethylstyrene.

Examples of dihydric aliphatic alcohols include ethylene glycol, propylene glycol, 1,2-, 1,3-, 1,4- or 2,3-butanediol, 1,5-pentanediol, neopentyl glycol, 1,6-hexanediol, trimethylpentanediol, hydrogenated bisphenol A, 1,4-cyclohexanedimethanol, diethylene glycol, dipropylene glycol and bifunctional polycaprolactone polyols such as PCL- 205 and PCL- 220 both sold by Daicel Chemical Industries, Ltd.

Examples of polyhydric alcohols having a functionality greater than two include trimethylolethane, trimethylolpropane, glycerine, pentaerythritol, di-trimethylolpropane, dipentaerythritol, sorbitol, trifunctional polycaprolactone polyols such as PCL- 305 and PCL- 308 both sold by Daicel Chemical Industries, Ltd., and tetrafunctional polycaprolactone polyols such as ε-caprolactone adducts of pentaerythritol or di-trimethylolpropane.

The second class of initiators includes a hydroxyl group-containing acrylic monomer of Formula VII:

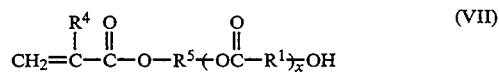

wherein $R^1$ and x are as defined above, $R^4$ is hydrogen atom or methyl, and $R^5$ is a $C_2$–$C_8$ alkylene. Specific examples of the acrylic monomers include hydroxyalkyl (meth)acrylates such as 2-hydroxyethyl (meth)acrylate, 2-hydroxypropyl(meth)acrylate, 3-hydroxypropyl(meth)acrylate and 4-hydroxybutyl(meth)acrylate. The term "(meth)acrylate" as used herein collectively refers to acrylate and methacrylate. Also included in this class of initiators are adducts of a hydroxyalkyl(meth)acrylate with a alkanoic lactone such as ε-caprolactone. Adducts of 2-hydroxyethyl(meth)acrylate with ε-caprolactone are commercially available from Daicel Chemical Industries, Ltd. as PCL- FA and FM series.

The third class of initiators includes acrylic polymers having a recurring unit of Formula VIII:

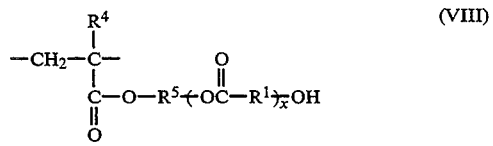

wherein $R^1$, $R^4$, $R^5$ and x are as defined above. The acrylic polymer initiator preferably consists of 5–95 mole % of the recurring unit of Formula VIII and the balance of another recurring unit corresponding to an ethylenically unsaturated comonomer. These acrylic polymer initiators may be produced by copolymerizing from 5 to 95 mole % of an acrylic monomer of Formula VII as described above and the balance of an ethylenically unsaturated comonomer other than the above monomer. Examples of comonomers include alkyl (meth)acrylates such as methyl, ethyl, n-propyl, isopropyl, n-butyl, sec.-butyl, t-butyl or 2-ethylhexyl (meth)acrylate, acrylonitrile, styrene, α-methylstryrene, vinyl acetate, vinyl propionate and the like. The polymerization may be carried out by the conventional solution polymerization technique.

The fourth class of initiators includes a polyester polyol having a functionality number from 2 to 15. As is well-known, polyesters are prepared by the polycondensation reaction of a polycarboxylic acid component and a polyhydric alcohol component. Examples of polycarboxylic acids include aromatic dicarboxylic acids and acid anhydrides such as terephthalic acid, isophthalic acid, phthalic acid, phthalic anhydride, 2,6-naphthalenedicarboxylic acid and 2,7-naphthalenedicarboxylic acid; aliphatic dicarboxylic acids such as succinic acid, adipic acid, azelaic acid, sebacic acid, dodecanedicarboxylic acid and 1,4-cyclohexanedicarboxylic acid; and tri- and tetracarboxylic acids such as trimellitic acid and pyromellitic acid. The polycondensation reaction is carried out using the polycarboxylic acid component and the polyhydric alcohol component in such a proportion that the resulting polyester polyol has at least two terminal hydroxyl groups.

Catalyst

Examples of catalysts usable in the process of the invention include Bronsted acids such as hydrogen fluoride, hydrogen chloride, sulfuric acid, p-toluenesulfonic acid, dodecylbenzenesulfonic acid, methanesulfonic acid, trifluoroacetic acid and trifluoromethanesulfonic acid; and Bronsted anion salts of onium of nitrogen, sulfur, phosphorus or iodine. Typical examples of such onium salts are listed below:

(i) Quarternary ammonium salts:
N,N-dimethyl-N-benzylanilinium hexafluoroantimonate;
N,N-diethyl-N-benzylanilinium tetrafluoroborate;
N-benzylpyridinium hexafluoroantimonate;
N-benzylpyridinium triflate;
N-(4-methoxybenzyl)pyridinium hexafluoroantimonate;
N,N-diethyl-N-(4-methoxybenzyl)toluidinium hexafluoroantimonate; and
N,N-dimethyl-N-(4-methoxybenzyl)toluidinium hexafluoroantimonate.

(ii) Sulfonium salts:
triphenylsulfonium tetrafluoroborate;
triphenylsulfonium hexafluoroantimonate;
triphenylsulfonium hexafluoroarsenate;
ADEKA CP-66(Asahi Denka Kogyo K.K.);
ADEKA CP-77(Asahi Denka Kogyo K.K.);
tri-(4-methoxyphenyl)sulfonium hexafluoroantimonate; and
diphenyl-(4-phenylthiophenyl)sulfonium hexafluoroantimonate.

(iii) Phosphonium salts:
ethyltriphenylphosphonium hexafluoroantimonate; and
tetrabutylphosphonium hexafluoroantimonate.

(iv) Iodonium salts:
diphenyliodonium hexafluoroantimonate;
di-4-chlorophenyliodonium hexafluoroantimonate;
di-p-tolyliodonium hexafluoroantimonate; and
phenyl-(4-methoxyphenyl)iodonium hexafluoroantimonate.

Anions of the above onium salts may be replaced by other Bronsted acid anions such as acetate, propionate, octanate, laurate, stearate, benzoate, benzensulfonate, toluenesulfonate, dodecylbenzenesulfonate Or perchlorate.

Examples of usable catalysts also include strongly acidic ion exchange resins such as Amberlist 15; alkyl alkali metals such as n-butyllithium and s-butyllithium; alkali metal alkoxides such as Li, Na or K ethoxide, butoxide, isobutoxide, t-butoxide or octyloxide; amines such as diethylamine, triethylamine, dibutylamine, N,N-dimethyl-cyclohexylamine, dimethylbenzylamine, hexamethylenetetramine and 1,8-diazabicyclo [5,4,0]-7-undecene; tin compounds such as dibutyltin oxide, dibutyltin dilaurate, monobutyltin trichloride, dibutyltin dichloride, tributyltinchloride, stannous chloride, stannous bromide and stannous iodide; tungsten compounds such as phosphortungstic acid and silicotungstic acid; titanium compounds such as titanium tetrabutoxide; and zinc compounds such as zinc chloride.

Ring-opening Reaction

The ring-opening reaction of the cyclic alkylenecarbonate for producing a linear carbonate may be performed by heating a mixture of a cyclic carbonate and an initiator to an elevated temperature up to 150° C. in the presence of a catalyst. Usually greater than 0.5 equivalents of the cyclic carbonate are used relative to each hydroxyl group possessed by the initiator. The amount of catalyst generally ranges between 1 ppm and 5%, preferably between 5 ppm and 5,000 ppm relative to the reaction mixture. The reaction may be carried out in an aprotic solvent. Examples of usable solvents include aromatic hydrocarbons such as benzene, toluene or xylene, esters such as ethyl acetate butyl acetate; ketones such as acetone or methyl isobutyl ketone; halogenated hydrocarbons such as dichloromethane or dichloroethane; ethers such as tetrahydrofuran or 1,4-dioxane; and other aprotic solvents such as acetonitrile, nitrobenzene or nitromethane. The above materials may be charged in a reaction vessel in any desired order but preferably in the order of the solvent, initiator, cyclic carbonate and catalyst. The reaction end point may be confirmed by measuring the concentration of the cyclic carbonate in the reaction mixture using any conventional technique such as gas chromatography. Normally, less than 1% concentration of the cyclic carbonate may be regarded as the end point. After the reaction the resulting linear carbonate may be recovered and purified in any conventional technique such as distillation, precipitation, recrystallization and the like.

Utility of Linear Carbonate

Glycol hemiesters such as ethylene glycol monoacetate are used as a solvent. Polycaprolactone or other polyols containing ester linkage are used, for example, in the polyurethane industry. However, the ester linkage is known to be susceptible to hydrolysis. The aliphatic linear carbonate of Formula I is refractory to hydrolysis and, therefore, finds use as a raw material for the production of water-resistant plastics such as polyurethane.

Hydroxyl group-containing acrylic polymers are used in the coating industry as a film-forming resin to be crosslinked with a melamine resin or organic polyisocyanate. It is known that the acrylic polymer becomes more reactive with the crosslinker if the hydroxyl group is spaced apart from the polymer backbone chain by a longer pendant group. The acrylic polymer having the recurring unit of Formula III meets these requirements. Additionally, since the hydroxyl group-bearing pendant group is bound to the polymer backbone through a chemically stable carbonate linkage, the acrylic polymer is refractory to hydrolysis. The same applies to the modified polyester polyol of Formula IV. For use as a film-forming resin, the acrylic polymer preferably contains from 5 to 95 mole % of the recurring unit of Formula III and has a number average molecular weight from 1,000 to 50,000 and more preferably from 1,500 to 25,000. The modified polyester polyol preferably has a number average molecular weight from 800 to 50,000 and more preferably from 1,200 to 25,000.

The modified acrylic monomer of Formula II may be used for the production of an acrylic polymer having the recurring unit of Formula III by copolymerizing with a suitable comonomer.

EXAMPLES

The following examples are intended to further illustrate the invention without limiting thereto. All parts and percents therein are by weight unless otherwise indicated.

Example 1

3.9 g of neopentyl glycol carbonate was dissolved in 4.44 g of n-butanol and 0.075 g of N-benzylpyridinium p-toluenesulfonate was added to the solution. The mixture was heated at 120° C. for 20 minutes. After the reaction, the mixture was evaporated in vacuo to remove unreacted butanol and then filtered to remove unreacted neopentyl glycol carbonate. Butyl 2,2-dimethyl-3-hydroxypropylcarbonate was obtained.

Example 2

11.7 g of neopentyl glycol carbonate was dissolved in 4.44 g of n-butanol and 0.075 g of N-benzylpyridinium p-toluenesulfonate was added to the solution. The mixture was heated at 120° C. for 4 hours. After the reaction, the mixture was evaporated in vacuo to remove unreacted butanol and then filtered to remove unreacted neopentyl glycol carbonate. A hydroxy-terminated linear polycarbonate was obtained.

Example 3

3.9 g of neopentyl glycol was reacted with 6.2 g of ethylene glycol by heating at 120° C. for 3 hours in the presence of 0,075 g of N-benzylpyridinium p-toluenesulfonate. After the reaction, the mixture was evaporated in vacuo to remove unreacted ethylene glycol and filtered to remove unreacted neopentyl glycol carbonate. A carbonate diol was obtained.

Example 4

15.6 g of neopentyl glycol carbonate was reacted with 6.2 g of ethylene glycol by heating at 120° C. for 7 hours in the presence of 0.13 g of α, α-dimethylbenzylpyridinium hexafluoroantimonate. After the reaction, the mixture was evaporated in vacuo to remove unreacted ethylene glycol and then filtered to remove unreacted neopentyl glycol carbonate. A polycarbonate polyol was obtained.

Example 5

3.9 g of neopentyl glycol carbonate was dissolved in 5.0 g of n-hexanol and 0.075 g of p-toluenesulfonic acid was added to the solution. The mixture was heated at 100° C. for 20 minutes. After the reaction, the mixture was evaporated in vacuo to remove unreacted n-hexanol and then filtered to remove unreacted neopentyl glycol carbonate. n-Hexyl 2,2-dimethyl-3-hydroxypropyl carbonate was obtained.

Example 6

A mixture of 7.8 g of neopentyl glycol carbonate, 15.9 g of PCL- 205 (bifunctional caprolactone oligomer sold by Daicel Chemical Industries, Ltd., MW=503, OH number=530), and 0.075 g of N-benzylpyridinium p-toluenesulfonate was heated at 120° C. for 4 hours. After the reaction, the mixture was poured in methanol to precipitate the desired polycarbonate polyol repeatedly. The hydroxyl number of the product was 141.

IR: 3450 cm$^{-1}$ (OH), 1720 cm$^{-1}$ (C=O)

Example 7

A mixture of 11.7 g of neopentyl glycol carbonate, 16.5 g of PCL- 305 (trifunctional caprolactone oligomer sold by Daicel Chemical Industries Ltd., MW=503, OH number=530), and 0.075 g of N-benzylpyridinium p-toluenesulfonate was heated at 120° C. for 7 hours. After the reaction, the mixture was poured in methanol to precipitated the desired polycarbonate polyol repeatedly. The hydroxyl number of the product was 179.

IR: 3450 cm$^{-1}$ (OH), 1715 cm$^{-1}$ (C=O)

Example 9

A four necked flask equipped with an air tube, thermometer, condenser and stirrer was charged with 1.371 g of 2-hydroxyethyl acrylate, 1.950 g of neopentyl glycol carbonate, 0,019 g of hydroquinone monomethyl ether and 0,003 g of stannous chloride. The mixture was allowed to react at 115° C. for 25 hours while bubbling with air. The $^1$H-NMR analysis was used to trace the reaction rate and indicated that 69.7% of neopentyl glycol carbonate was consumed in the reaction. The hue of the product was 100 (APHA).

The GPC pattern of the product indicated that the product was a mixture of unreacted neopentyl glycol carbonate (28.789 min.), unreacted 2-hydroxyethyl acrylate (28.277 min.), 2-hydroxyethyl acrylate/neopentyl glycol adducts at a molar ratio 1:1 (26,237 min.), 1:2 (25,145 min.), 1:3 (24.415 min.) and higher adducts.

In $^1$H-NMR, various peaks were assigned as follows:

0.938–1.011 ppm, methyl in linear neopentyl glycol carbonate chain;

1.139 ppm, methyl in unreacted neopentyl glycol carbonate;

3.358–3.374 ppm, methylene adjacent to the terminal OH in the adduct;

3.819–3,877 ppm and 4.292–4.343 ppm, methylene in unreacted 2-hydroxyethyl acrylate;

3.968–4.015 ppm, methylene in linear neopentyl glycol carbonate chain;

4.079 ppm, methylene in unreacted neopentyl glycol carbonate;

4.389–4,441 ppm, methylene of acrylate ester moiety in the adduct; and 5.853–6.574 ppm, acryl in unreacted acrylate and the adduct.

The above data supported the composition of the product to be mainly consisted of an adduct of 2-hydroxyethyl acrylate and neopentyl glycol carbonate at a molar ratio of 1:2.

Example 10

The same flask as used in Example 9 was charged with 1.950 g of 2-hydroxyethyl methacrylate, 1.950 g of neopentyl glycol carbonate, 0.019 g of hydroquinone monomethyl ether and 0.004 g of hydroxybutyltin oxide. The mixture was allowed to react at 115° C. for 27 hours while bubbling with air. The reaction rate was traced by the $^1$H-NMR analysis. 89.8% of neopentyl glycol carbonate had reacted at the end of reaction. The hue was 120 (APHA).

Example 11

The same flask as used in Example 9 was charged with 1.371 g of 2-hydroxyethyl acrylate, 1.950 g of neopentyl glycol carbonate, 0.019 g of hydroquinone monomethyl ether and 0.003 g of p-toluenesulfonic acid. The mixture was allowed to react at 115° C. for 25 hours. The reaction rate was traced by the $^1$H-NMR analysis. 95.7% of neopentyl glycol carbonate had reacted at the end of reaction. The hue was 100 (APHA).

Example 12

The same flask as used in Example 9 was charged with 1.371 g of 2-hydroxyethyl acrylate, 1,949 g of neopentyl glycol carbonate, 0.019 g of hydroquinone monomethyl ether and 0,003 g of sodium ethoxide. The mixture was allowed to react at 115° C. for 25 hours. The reaction rate was traced by the $^1$H-NMR analysis. 79.6% of neopentyl glycol carbonate had reacted at the end of reaction. The hue was 90 (APHA).

Example 13

The same flask as used in Example 9 was charged with 1.371 g of 2-hydroxyethyl acrylate, 1.949 g of neopentyl glycol carbonate, 0.019 g of hydroquinone monomethyl ether and 0.009 g of triethylamine. The mixture was allowed to react at 115° C. for 25 hours. The reaction rate was traced by the $^1$H-NMR analysis. 62.4% of neopentyl glycol had reacted at the end of reaction. The hue was 120 (APHA).

Example 14

The same flask as used in Example 9 was charged with 2.6 g of 2-hydroxyethyl methacrylate, 2.6 g of neopentyl glycol carbonate, 0.026 g of hydroquinone monomethyl ether and 0,038 g of p-toluenesulfonic acid monohydrate. The mixture was allowed to react at 40° C. for 120 minutes while bubbling with air. The $^1$H-NMR and IR spectra of the product revealed that the product consisted mainly of an adduct of 2-hydroxyethyl methacrylate and neopentyl glycol carbonate at a molar ratio of 1:2.

Example 15

The same flask as used in Example 9 was charged with 5.2 g of 2-hydroxypropyl acrylate, 5.2 g of neopentyl glycol carbonate, 0.052 g of hydroquinone monomethyl ether and 0,076 g of p-toluenesulfonic acid monohydrate. The mixture was allowed to react at 40° C. for 18 hours while bubbling air through it. The $^1$H-NMR and IR spectra revealed that the product was consisted mainly of an adduct of 2-hydroxypropyl acrylate and neopentyl glycol carbonate at a molar ratio of 1:1.

Example 16

The same flask as used in Example 9 was charged with 2.88 g of 4-hydroxybutyl acrylate, 2.6 g of neopentyl glycol carbonate, 0,027 g of hydroquinone monomethyl ether and 0.038 g of p-toluenesulfonic acid monohydrate. The mixture was allowed to react at 40° C. for 60 minutes with stirring and air-bubbling. The $^1$H-NMR and IR spectra revealed that the product was consisted mainly of an adduct of 4-hydroxybutyl acrylate and neopentyl glycol carbonate at a molar ratio of 1:2.

Example 17

The same flask as used in Example 9 was charged with 12.688 g of PCL- FM-1 (Daicel Chemical Industires, Ltd.), 3.414 g of neopentyl glycol carbonate and 0.049 g of p-toluenesulfonic acid monohydrate. The mixture was allowed to react at 40° C. for 60 minutes with stirring. After the reaction, the mixture was cooled and filtered to remove precipitated solids. The $^1$H-NMR and IR spectra revealed that the product was consisted mainly of an adduct of PCL-FM-1 and neopentyl glycol carbonate at a molar ratio of 1:1.

Example 18

Example 17 was repeated except that 0.049 g of AMBERLIST 15 was replaced for p-toluenesulfonic acid monohydrate. The same product was obtained.

Example 19

A flask was charged with 4.8 g of butanol and heated to 120°C. To this was added dropwise a mixture of 2.8 g of styrene, 12.0 g of the modified acrylic monomer produced in Example 17 and 1.2 g of t-butyl peroctoate over 2 hours. After the addition, the mixture was maintained at 120° C. for 3 hours to complete the reaction. The resulting polymer solution was poured in methanol to precipitate the polymer repeatedly. The polymer was characterized by the following date;

Mn=19,900; Mw/Mn=1.9; OH number=99(mg KOH/g)

IR: 3450 cm$^{-1}$ (OH); 1745 cm$^{-1}$ (O-CO-O); 1720 cm$^{-1}$ (COO)

Production Example 1

A flask was charged with 19.2g of xylene and 4.8 g of butanol, and heated to 120°C. To this was added dropwise a mixture of 28.0 g of styrene, 12.0 g of 2-hydroxyethyl methacrylate and 1.2 g of t-butyl peroctoate over 2 hours. After the addition, the mixture was maintained at 120° C. for 3 hours to complete the reaction. The resulting polymer solution was poured in methanol to precipitate the polymer repeatedly. The polymer named Polymer A was characterized by the following data.

Mn=13,000; Mn/Mn=1.7; OH number=131 (mg KOH/g)

Production Example 2

A flask was charged with 19.2 g of xylene and 4.8 g of butanol, and heated to 100°C. To this was added dropwise a mixture of 28.0 g of methacrylic acid, 12.0 g of 2-hydroxyethyl methacrylate and 1.2 g of t-butyl peroctoate over 2 hours. After the addition, the mixture was maintained at 100° C. for 3 hours. The resulting polymer solution was poured in methanol to precipitate the polymer repeatedly. The polymer named Polymer B was characterized by the following data:

Mn=18,000; Mw/Mn=1.8; OH numner=131( mg KOH/g)

Production Example 3

A flask was charged with 19.2g of xylene and 4.8g of butanol, and heated to 100°C. To this was added a mixture of 20 g of methyl methacrylate, 8.0 g of styrene, 6 g of n-butyl acrylate, 6 g of 2-hydroxyethyl methacrylate and 0.6 g of t-butyl peroctoate over 2 hours. After the addition, the mixture was maintained at 100° C. for 3 hours to complete the reaction and then poured in methanol to precipitate a polymer repeatedly. The polymer named Polymer C was characterized by the following data:

Mn=22,000; Mw/Mn=1.9; OH number=65 (mg KOH/g)

Production Example 4

A flask was charged with 19.2 g of xylene and 4.8 g of butanol, and heated to 130°C. To this was added dropwise a mixture of 20 g of methyl methacrylate, 8.0 g of styrene, 6 g of n-butyl acrylate, 6 g of 2-hydroxyethyl methacrylate and 1.2 g of t-butyl peroctoate over 2 hours. After the addition, the mixture was maintained at 130° C. for 3 hours to complete the reaction and then poured into methanol to precipitate a polymer repeatedly. The polymer named Polymer D was. characterized by the following data:

$Mn=10,200$; $Mw/Mn=1.7$; OH number=60 (mg KOH/g)

Production Example 5

A flask was charged with 19.2 g of xylene and 4.8 g of butanol, and heated to 130°C. To this was added dropwise a mixture of 20 g of methyl methacrylate, 8.0 g of styrene, 6 g of n-butyl acrylate, 6 g of 2-hydroxyethyl methacrylate and 2.0 g of t-butyl peroctoate over 2 hours. After the addition, the mixture was maintained at 130° C. for 3 hours to complete the reaction and then poured in methanol to precipitate a polymer repeatedly. The polymer named Polymer E was characterized by the following data:

$Mn=8,500$; $Mw/Mn=1.7$; OH number=63 (mg KOH/g)

Production Example 6

A flask was charged with 19.2 g of xylene and 4.8 g of butanol, and heated to 130°C. To this was added dropwise a mixture of 20 g of methyl methacrylate, 8.0 g of styrene, 6 g of n-butyl acrylate, 6 g of 2-hydroxyethyl methacrylate, 0.5 g of methacrylic acid and 2.0 g of t-butyl peroctoate over 2 hours. After the addition, the mixture was maintained at 130° C. for 3 hours to complete the reaction and then poured in methanol to precipitate a polymer repeatedly. The polymer named Polymer F was characterized by the following data:

$Mn=8,200$; $Mw/Mn=1.7$; OH number=63 (mg KOH/g);

acid number=8 (mg KOH/g)

Example 20

10 g of Polymer A was dissolved in 10 g of toluene with heating. To this were added 3.0 g of neopentyl glycol carbonate and 0.044 g of p-toluenesulfonic acid monohydrate. The mixture was allowed to react at 120° C. for 90 minutes and then .poured in methanol to isolate a modified polymer having the following characterizing data:

$Mn=19,900$; $Mw/Mn=1.9$; OH number=99 (mg KOH/g);

IR : 3450 $cm^{-1}$ (OH), 1745 $cm^{-1}$ (O-CO-O), 1720 $cm^{-1}$ (COO)

Example 21

10 g of Polymer B was dissolved in 10 g of toluene with heating. To this were added 3.0 g of neopentyl glycol carbonate and 0,004 g of p-toluenesulfonic acid monohydrate. The mixture was allowed to react at 100° C. for 60 minutes and then poured in methanol to isolate a modified polymer having the following characterizing data:

$Mn=19,000$; $Mw/Mn=1.9$; OH number=99 (mg KOH/g);

IR: 3450 $cm^{-1}$ (OH), 1745 $cm^{-1}$ (O-CO-O), 1720 $cm^{-1}$ (COO)

Example 22

10 g of Polymer C was dissolved in 10 g of toluene with heating. To this were added 3.0 g of neopentyl glycol carbonate and 2 g of AMBERLIST 15. The mixture was allowed to react at 80° C. for 90 minutes and then poured in methanol to isolate a modified polymer having the following characterizing data:

$Mn=24,000$; $Mw/Mn=2.1$; OH number=50 (mg KOH/g);

IR: 3450 $cm^{-1}$ (OH), 1745 $cm^{-1}$ (O-CO-O), 1720 $cm^{-1}$ (COO)

Example 23

10 g of Polymer E was dissloved in 10 g of toluene with heating. To this were added 3.0 g of neopentyl glycol carbonate and 1.0 g of AMBERLIST 15. The mixture was allowed to react at 80° C. for 90 minutes and then poured in methanol to isolate a modified polymer having the following characterizing data:

$Mn=11,500$; $Mw/Mn=1.9$; OH number=45 (mg KOH/g);

IR: 3450 $cm^{-1}$ (OH), 1745 $cm^{-1}$ (O-CO-O), 1720 $cm^{-1}$ (COO)

Example 24

10 g of Polymer E was dissolved in 10 g toluene with heating. To this were added 3.0 g of neopentyl glycol carbonate and 1.5 g of AMBERLIST 15 E. The mixture was allowed to react at 80° C. for 30 minutes and then poured in methanol to isolate a modified polymer having the following characterizing data:

$Mn=10,000$; $Mw/Mn=1.9$; OH number=47 (mg KOH/g);

IR: 3450 $cm^{-1}$ (OH), 1745 $cm^{-1}$ (O-CO-O), 1720 $cm^{-1}$ (COO)

Example 25

10 g of Polymer E was dissolved in 10 g toluene with heating. To this were added 1.5 g of neopentyl glycol carbonate and 1.5 g of AMBERLIST 15 E. The mixture was allowed to react at 80° C. for 30 minutes and then poured in methanol to isolate a modified polymer having the following characterizing data:

$Mn=9,300$; $Mw/Mn=1.8$; OH number=47 (mg KOH/g);

IR : 3450 $cm^{-1}$ (OH), 1745 $cm^{-1}$ (O-CO-O), 1720 $cm^{-1}$ (COO)

Example 26

10 g of Polymer F was dissolved in 10 g toluene with heating. To this were added 1.5 g of neopentyl glycol carbonate and 1.5 g of AMBERLIST 15 E. The mixture was allowed to react at 80° C. for 30 minutes and then poured in methanol to isolate a modified polymer having the following characterizing data:

Mn=9,300; Mw/Mn=1.8; OH number=47 (mg KOH/g);

IR : 3450 cm$^{-1}$ (OH), 1745 cm$^{-1}$ (O-CO-O), 1720 cm$^{-1}$ (COO)

Production Example 7

A reactor equipped with a heater, stirrer, reflux condenser, water separator, distiller and thermometer was charged with 222 parts of trimethylolpropane, 319 parts of neopentyl glycol and 188 parts of 1,6-hexanediol, and heated to 80°-120°C. Stirring was started when the mixture became a solution. To this were added 707 parts of isophthalic acid and 155 parts of adipic acid. Then the temperature was raised to 180° C. until water began to evolve. Thereafter, the temperature was raised to 230° C. at a constant rate over 3 hours while removing water from the reaction system and then maintained at 230° C. for 2 hours. Then, xylene was added to the reactor and the reaction was continued while removing water by the azeotropic distillation with xylene until an acid number of 15 was reached. After cooling, the reaction mixture was dilluted with 600 parts of xylene. A polyester varish named Polyester A having a nonvolatile content of 70.4%, an acid number of 10.4 mg KOH/g, and a hydroxyl number of 150 mg KOH/g was obtained.

IR: 3450 cm$^{-1}$ (OH), 1720 cm$^{-1}$ (COO)

Production Example 8

The same reactor as used in Production Example 7 was charged with 324 parts of trimethylolpropane, 165 parts of 1,5 pentanediol and 134 parts of 1,6-hexanediol, and heated to 80°-120°C. Stirring was started when the mixture became a solution. To this were added 356 parts of phthalic anhydride and 399 parts of isophthalic acid. Then the temperature was raised to 180° C. until water began to evolve. Thereafter, the temperature was raised to 230° C. at a constant rate over 3 hours while removing water from the reaction system and then maintained at 230° C. for 2 hours. Then xylene was added to the reactor and the reaction was continued while removing water by the azeotropic distillation with xylene until an acid number of 8 was reached. After cooling, the raction mixture was diluted with 810 parts of xylene. A polyester varnish named Polyester B having a nonvolatile content of 60.4%, an acid number of 5 mg KOH/g and a hydroxyl number of 140 mg KOH/g was obtained.

IR: 3450 cm$^{-1}$ (OH), 1720 cm$^{-1}$ (COO)

Example 27

10 g of Polyester A was reacted with 3.0 g of neopentyl glycol carbonate in the presence of 0.044 g of p-toluenesulfonic acid monohydrate at 120° C. for 90 minutes. After the reaction, the product was poured in methanol repeatedly to isolate a modified polyester polyol having the following characterizing data:

OH number=100 mg KOH/g; acid number=6 mg KOH/g;

IR: 3450 cm$^{-1}$ (OH), 1745 cm$^{-1}$ (O-CO-O), 1720 cm$^{-1}$ (COO)

Example 28

10 g of Polyester B was reacted with 3.0 g of neopentyl glycol carbonate in the presence of 2 g of AMBERLIST 15 (H-form) at 70° C. for 30 minutes. After the reaction, the product was poured in methanol repeatedly to isolate a modified polyester polyol having the following characterizing data:

OH number=105 mg KOH/g; acid number=7 mg KOH/g;

IR: 3450 cm$^{-1}$ (OH), 1745 cm$^{-1}$ (O-CO-O), 1720 cm$^{-1}$ (COO)

We claim:

1. A modified polyester polyol of the formula:

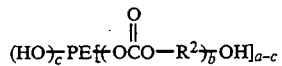

wherein PE is the residue of a polyester polyol with removal of hydroxyl groups, a is an integer of 2-15, b is an integer of 1-6, and c is an integer satisfying the relationship : $0 \leq c < a$.

2. The modified polyester polyol according to claim 1 which is a reaction product of a polyester polyol having a functionality of 2-15 with neopentyl glycol carbonate, the number average molecular weight of said modified polyester polyol being from 800 to 50,000.

3. A process for producing a modified polyester polyol of claim 1 comprising reacting a polyester polyol having a functionality number of from 2 to 15 with a $C_2$-$C_8$ alkylene glycol carbonate forming a 5-7 membered ring, in the presence of a catalyst selected from the group consisting of a Bronsted acid, an onium salt thereof, a strongly acid ion exchange resin, an alkyl alkali metal, an alkali metal alkoxide, an amine, a tin compound, a tungsten compound, a titanium compound, and a zinc compound.

4. The process according to claim 4, wherein said alkylene glycol carbon is neopentyl glycol carbonate.

5. A compound of claim 1, wherein PE is the residue of the reaction product of a polycondensation reaction of a polycarboxylic acid selected from the group consisting of terephthalic acid, isophthalic acid, phthalic acid, 2,6-naphthalenedicarboxylic acid, 2,7-naphthalenedicarboxylic acid, succinic acid, adipic acid, azelaic acid, sebacic acid, dodecanedicarboxylic acid, 1,4-cyclohexane-dicarboxylic acid, trimellitic acid and pyromellitic acid and a polyhydric alcohol, in such a proportion that the resulting polyester polyol has at least two terminal hydroxyl groups.

* * * * *